US00PP13007P2

(12) United States Plant Patent
Jobling

(10) Patent No.: US PP13,007 P2
(45) Date of Patent: Sep. 24, 2002

(54) VERBENA PLANT NAMED 'DOSMAU'

(76) Inventor: Beres Jobling, P.O. Box 26 Haartcheeshoek 498JQ, Skeerport, Magaliesberg (ZA), 0232

( * ) Notice: Subject to any disclaimer, the term of this patent is extended or adjusted under 35 U.S.C. 154(b) by 34 days.

(21) Appl. No.: 09/590,358

(22) Filed: Jun. 8, 2000

(51) Int. Cl.[7] ..... A01H 5/00

(52) U.S. Cl. ..... Plt./308

(58) Field of Search ..... Plt./308

*Primary Examiner*—Bruce R. Campell
*Assistant Examiner*—Michelle Kizilkaya

(57) ABSTRACT

A new cultivar of Verbena named 'Dosmau' that is characterized by its spreading growth habit with dense foliage coverage and by its bright pink flowers with a distinct white eye zone. The flowers fade in color to give a multi-colored pink flower cluster.

3 Drawing Sheets

CROSS-REFERENCE TO RELATED APPLICATIONS

The application for this new invention will be co-pending with two other applications corresponding to plants that were derived from the same breeding program. They are entitled: Verbena Plant Named 'Dospi' (application Ser. No. 09/590,359) and Verbena Plant Named 'Dosblu' (application Ser. No. 09/590,360). However, 'Dosmau', 'Dosblu' and 'Dospi' are not known to be genetically related since the parents chosen for each cross were unique.

BACKGROUND OF THE INVENTION

The present invention relates to a new and distinct cultivar of *Verbena peruviana,* a perennial that is grown as a bedding and container plant. The new invention will be referred to hereinafter by the cultivar name 'Dosmau'.

The new Verbena is a selection from a breeding program conducted by the inventor in Skeerpoort, Magaliesberg, South Africa. The objective of the program is to select new cultivars of *Verbena peruviana* that have an improved habit combined with unique flower colors. 'Dosmau' and its co-pending varieties are especially characterized by their flower colors with prominent white eyes and their dense, spreading habit. 'Dosmau' was a seedling from a hand-pollinated cross made between Verbena 'Mauve' (unpatented) and Verbena 'Pink with Eye' (unpatented). The crossing and selection was done by the inventor in Skeerpoort, Magaliesberg, South Africa. The initial cross was made in February, 1996 and 'Dosmau' was selected in August, 1996. 'Dosmau' differs from its parents in that it has a more dense and well-branched habit than either of its parents. 'Dosmau' has a prominent white eye, whereas Verbena 'Mauve', which has similar flower color, has no white eye. The combined characteristics of the new invention, 'Dosmau', are unique. 'Dosmau' differs from another Verbena on the market known as Verbena 'Violet'. Verbena 'Violet' has a more open habit in the center of the plant when grown in a container, is less branched and has flower color that is violet with no eye. 'Dosmau' differs from the co-pending white-eyed variety, 'Dospi' in that 'Dospi' has flowers that are a brighter and different shade of pink and the foliage of 'Dosmau' is more pubescent than that of 'Dospi'. 'Dospi' is more variable in flower color as it fades.

Asexual reproduction of the new cultivar was first accomplished by taking terminal cuttings in Skeerpoort, Magiesberg, South Africa in August, 1996 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar from other commercial varieties.

1. The flower color of 'Dosmau' is mauve pink with a distinct white eye, 0.3–0.5 mm in diameter. No other Verbena known to the inventor with this flower color has a distinct white eye.

2. The color of the flower of 'Dosmau' fades as the flower ages giving a multi colored effect to the blossom. This effect is not as pronounced as it is for 'Dospi'.

3. The habit of 'Dosmau' is mounded and then spreading.

4. 'Dosmau' plants are well branched with short internodes to give the plant a dense appearance. Many verbenas of the trailing types do not have this dense coverage of foliage.

5. The foliage of 'Dosmau' is pubesecent.

BRIEF DESCRIPTION OF THE DRAWING

The accompanying drawings illustrate the distingquishing traits and overall appearance of the new Verbena cultivar 'Dosmau'. The plants are 9 months old from cuttings, in three-gallon containers and were grown outdoors in Encinitas, Calif.

Drawing 1 is of 'Dosmau' and the flower color, plant habit, and dense foliage characteristics can be observed.

A close-up of the flowers is shown in Drawing 2.

'Dosmau' is shown to the right of Verbena 'Violet' in Drawing 3. This drawing illustrates the dense habit of 'Dosmau' in comparison to Verbena 'Violet'. The prints were made from Fuji Provia slides and are as accurate as possible by conventional photography.

BOTANICAL DESCRIPTION OF THE PLANT

The following is a detailed description of the Verbena plant named 'Dosmau'. The data was collected from 9 month old plant grown in a three gallon container under outdoor conditions in Encinitas. Calif. Phenotypic differences may be observed with variations in environmental, climatic, and cultural conditions. The color determination is in accordance with The R.H.S. Colour Chart of The Royal Horticultural Society, London, England, except where general color items of ordinary dictionary significance are used.

Botanical classification: 'Dosmau' is a cultivar of *Verbena peruviana.*

Commercial classification: Verbena grown for bedding, container planting and for hanging baskets.

Parentage: Seedling selection from crosses made between Verbena 'Mauve' and Verbena 'Pink With Eye', both are selections of *Verbena peruviana.*

Plant description:

*Plant habit.*—Upright and then cascading.

*Height and spread.*—Up to 40 cm in height, up to 60 cm in spread.

*Type.*—Asexually propagated perennial, treated as annual in USDA hardiness zones 7 and colder.

*Root system.*—Fibrous, well branched, strong rooting habit.

*Propagation.*—Cuttings. Cuttings receive one pinch and are ready for transplanted in 3–4 weeks. 3 cuttings are used to finish a one-gallon basket container.

Diseases and pests: No known Verbena diseases observed.

Stems:

*Shape.*—Tetragonal.

*Size.*—Main stems up to 3 mm in diameter.

*Internode length.*—0.5–2.0 cm.

*Color.*—146A with a reddish brown anthocyanin pigmentation which appears as the stem ages, either in streaks or occasionally all around the stem.

*Surface.*—Short hairs.

Leaves:

*Shape.*—Ovate-Oblong.

*Division.*—Simple.

*Base.*—Cuneate.

*Apex.*—Acute.

*Venation.*—Not prominent.

*Margins.*—Crenate.

*Arrangement.*—Opposite.

*Surface.*—Upper: pubescent. Lower: pubescent.

*Length.*—Average 4 cm.

*Width.*—Average 2–3 cm.

*Color.*—Upper surface 137B, lower surface 147B.

*Petiole length.*—1.8–3.5 mm.

*Petiole width.*—2 mm in width.

*Petiole color.*—147B.

Flowers clusters:

*Type.*—Semi-rounded raceme-like umbel.

*Number.*—25–30/cluster.

*Flower cluster width.*—5.5–6.5 cm

*Flower cluster height.*—3.5–5.0 cm (averages).

*Stems.*—5–7 cm.

Perianth:

*Type.*—Salviform, fused at base.

*Margins.*—Entire.

*Texture.*—Smooth.

*Facingdirection.*—Upward.

*Number.*—5.

*Size.*—Height: 2.2 cm. Width: 2.0 cm. Individual Petal Length: 0.8–0.9 cm. Individual Petal Width: 0.6–0.8 cm. Eye Diameter: 0.3–0.5 mm.

*Color.*—Bud: 81A. Opening: 81A (flushed with 87A). Mature: 81B fading to 81A. Throat: 144C. Eye: 155D (more white).

Lastingness of the flowers and the umbel: Individual flowers last approximately 8 days The last individual flower to open in each umbel opens approximately 20 days after the first flower to open. The outer flowers open first.

Calyx: Gamosepalous, 5 sepals, 0.12–14 mm in length, 2.5–3.0 cm in width, 147B in color.

Reproductive organs:

*Stamens.*—4 in number.

*Stamen color.*—145B.

*Pistil.*—1 in number.

*Pistil color.*—145B.

Seed production:

*Quantity of seed.*—Usually 6 fertile seeds per capsule.

*Seed color.*—Light Brown.

*Shape of seed.*—Almost rectangular.

*Seed dimensions.*—5 mm length and 1 mm in width.

I claim:

1. A new and distinct cultivar of Verbena plant named 'Dosmau' as described and illustrated.

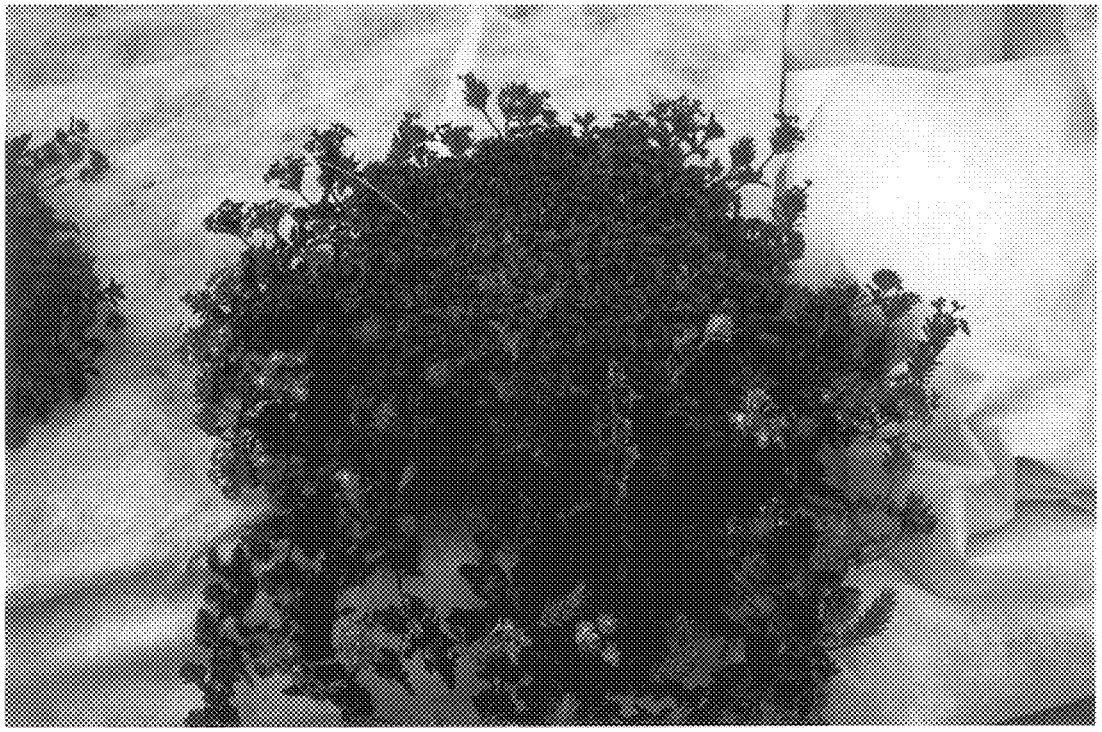

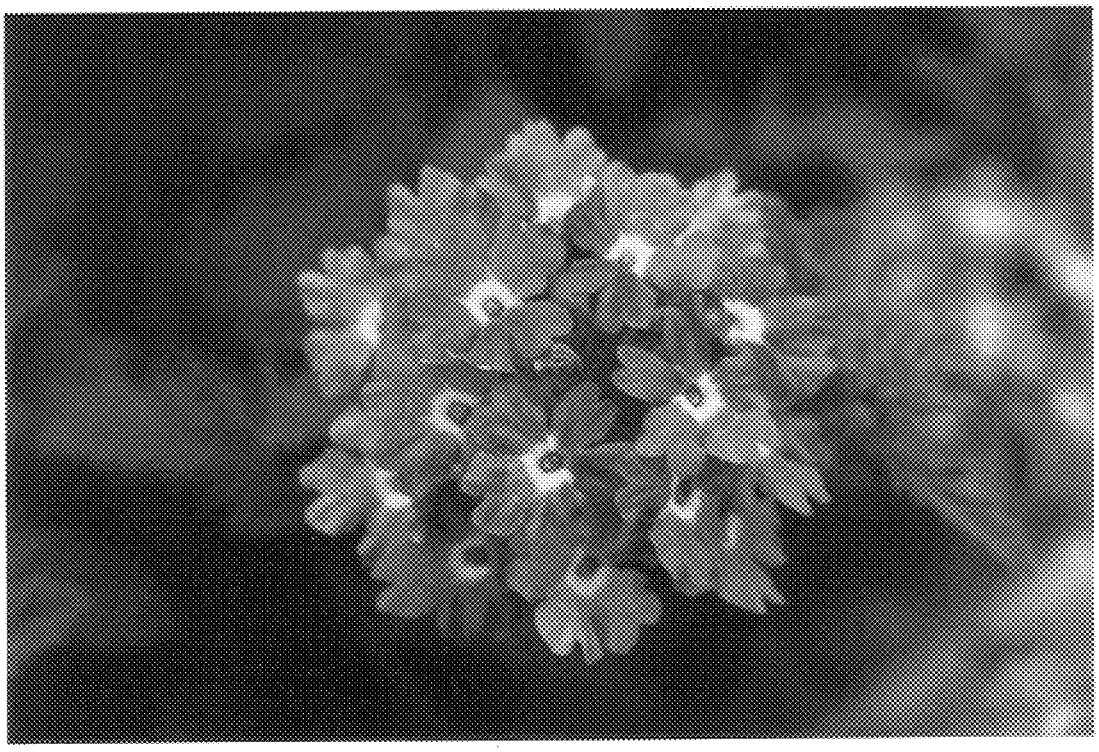

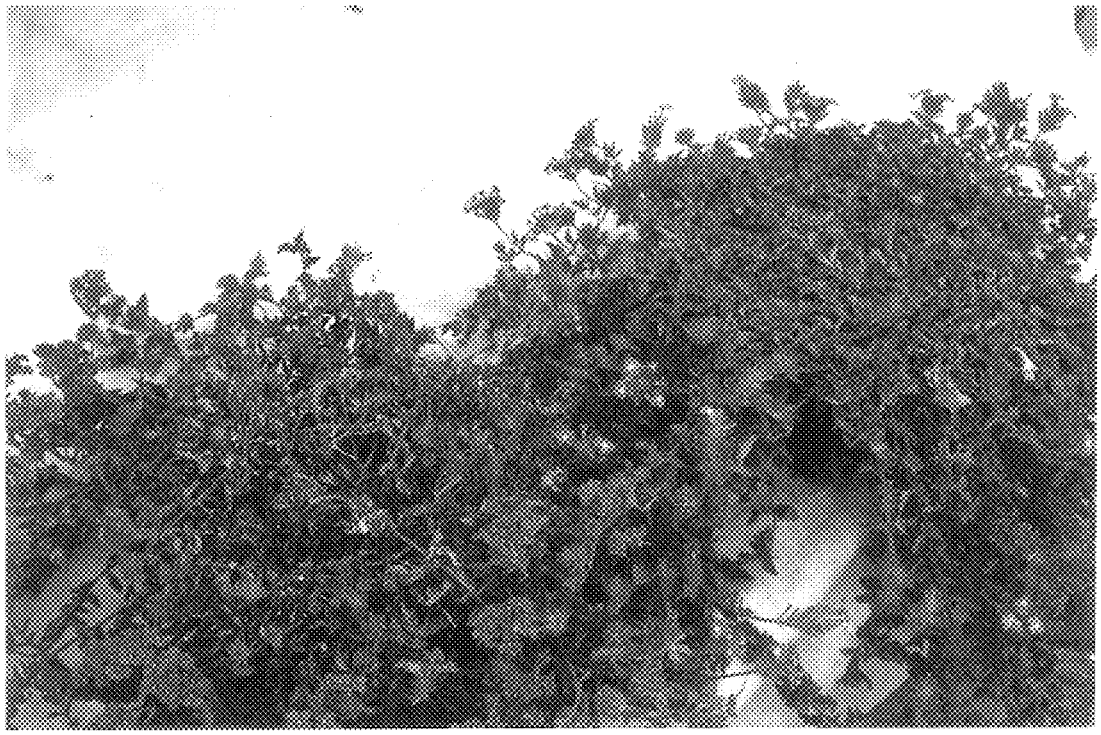

* * * * *